United States Patent
Jong (10) Patent No.: US 9,905,007 B2
(45) Date of Patent: Feb. 27, 2018

(54) DIGITAL SET TOP BOX (STB) HAVING A MULTIPLE IDENTIFICATION SYSTEM FOR TRANSMITTING PHYSIOLOGICAL INFORMATION APPLIED TO HETEROGENEOUS NETWORKS

(71) Applicant: National Kaohsiung University of Applied Sciences, Kaohsiung (TW)

(72) Inventor: Gwo-Jia Jong, Kaohsiung (TW)

(73) Assignee: National Kaohsiung University of Applied Sciences, Kaohsiung (TW)

( * ) Notice: Subject to any disclaimer, the term of this patent is extended or adjusted under 35 U.S.C. 154(b) by 50 days.

(21) Appl. No.: 15/008,522

(22) Filed: Jan. 28, 2016

(65) Prior Publication Data

US 2017/0221209 A1    Aug. 3, 2017

(51) Int. Cl.
| | | |
|---|---|---|
| *A61B 5/00* | (2006.01) | |
| *A61B 5/01* | (2006.01) | |
| *A61B 5/024* | (2006.01) | |
| *G06T 7/00* | (2017.01) | |
| *G01J 5/00* | (2006.01) | |

(52) U.S. Cl.
CPC .......... *G06T 7/0016* (2013.01); *A61B 5/0022* (2013.01); *A61B 5/01* (2013.01); *A61B 5/015* (2013.01); *A61B 5/024* (2013.01); *A61B 5/0013* (2013.01); *A61B 5/0077* (2013.01); *A61B 5/7278* (2013.01); *G01J 2005/0077* (2013.01); *G06T 2207/10016* (2013.01); *G06T 2207/10048* (2013.01); *G06T 2207/30101* (2013.01); *G06T 2207/30104* (2013.01)

(58) Field of Classification Search
CPC ......... G06T 7/0016; G06T 2207/10016; G06T 2207/10048; G06T 2207/30101; G06T 2207/30104; A61B 5/0022; A61B 5/01; A61B 5/015; A61B 5/024; A61B 5/0013; A61B 5/0077; A61B 5/7278; G01J 2005/0077
See application file for complete search history.

(56) References Cited

U.S. PATENT DOCUMENTS

| | | |
|---|---|---|
| 8,855,384 B2 | 10/2014 | Kyal et al. |
| 9,036,877 B2 | 5/2015 | Kyal et al. |
| 2008/0045847 A1* | 2/2008 | Farag .................. A61B 5/02055 600/500 |

(Continued)

*Primary Examiner* — Jon Chang
(74) *Attorney, Agent, or Firm* — Alan D. Kamrath; Kamrath IP Lawfirm, P.A.

(57) ABSTRACT

A physiological information detection system includes an image-capturing unit, an image-processing unit and a data-transmitting unit. The image-capturing unit is provided to capture a series of images of head portions and connects with the image-capturing unit to receive the captured images. The image-processing unit is operated to process the captured images and to trace a head portion area and a neck portion area thereof in the processed images. The image-processing unit is further operated to process the captured images to retrieve temperature data from the selected head portion area and the selected neck portion area. The image-processing unit is further operated to convert variations of the temperature data into estimated pulse data. The data-transmitting unit connects with the image-processing unit to transmit the estimated pulse data to a predetermined device.

20 Claims, 5 Drawing Sheets

(56) References Cited

U.S. PATENT DOCUMENTS

| | | | |
|---|---|---|---|
| 2014/0074493 A1* | 3/2014 | Schneider | G06F 19/3406 705/2 |
| 2014/0367256 A1* | 12/2014 | Terashima | A61B 5/0022 204/403.01 |
| 2015/0250391 A1 | 9/2015 | Kyal et al. | |

* cited by examiner

DIGITAL SET TOP BOX (STB) HAVING A MULTIPLE IDENTIFICATION SYSTEM FOR TRANSMITTING PHYSIOLOGICAL INFORMATION APPLIED TO HETEROGENEOUS NETWORKS

BACKGROUND OF THE INVENTION

1. Field of the Invention

The present invention relates to a thermal video-image physiological information detection system and method thereof for estimating pulse rates. Particularly, the present invention relates to a digital set top box (STB) having a multiple identification system for transmitting physiological information applied to heterogeneous networks.

2. Description of the Related Art

US Patent Application Publication No. 20150250391, entitled "Cardiac Pulse Rate Estimation from Source Video Data," discloses a system and method for estimating a cardiac pulse rate from a video of a subject being monitored for cardiac function. In one embodiment, batches of overlapping image frames are continuously received and processed by isolating regions of exposed skin. Pixels of the isolated regions are processed to obtain a time-series signal per region, and a physiological signal is extracted from each region's time-series signals. The physiological signal is processed to obtain a cardiac pulse rate for each region. The cardiac pulse rate for each region is compared to a last good cardiac pulse rate from a previous batch to obtain a difference. If the difference exceeds a threshold, the cardiac pulse rate is discarded. Otherwise, it is retained. Once all the regions have been processed, the retained cardiac pulse rate with a minimum difference becomes the good cardiac pulse rate for comparison on a next iteration.

Another U.S. Pat. No. 9,036,877, entitled "Continuous Cardiac Pulse Rate Estimation from Multi-channel Source Video Data with Mid-point Stitching," discloses a system and method for extracting PPG signals on a continuous basis from signals generated from video images captured of a subject being monitored for cardiac function in a non-contact remote sensing environment. In one embodiment, a time-series signal is received. The time-series signal is generated from video images captured of a region of exposed skin where a PPG signal of a subject of interest can be registered. The time-series signal is then divided into batches for processing, with successive batches having at least a 95% overlap with a previous batch. Each of the batches of time-series signals is processed to obtain a PPG signal from each batch. A mid-point of each of these PPG-signals is stitched together to obtain a continuous PPG signal for the subject. The continuous PPG signal for the subject can then viewed on a display device.

Another U.S. Pat. No. 8,855,384, entitled "Continuous Cardiac Pulse Rate Estimation from Multi-channel Source Video Data," discloses a computationally efficient system and method for estimating a subject's cardiac pulse rate from multi-channel source video data. In one embodiment, a time-series signal is continuously processed by repeatedly: (1) conditioning the estimated source signal obtained on a previous iteration to produce a next reference signal; and (2) using this reference signal to perform a constrained source separation on this next segment to obtain an estimated source signal. A frequency at which this next estimated source signal converged is the subject's estimated cardiac pulse rate for this signal segment. The reference signal is repeatedly updated. Upon convergence, the sliding window is shifted to define a next segment of the time-series signal. The method repeats for each time-series signal segment on a continuous basis or until a termination criteria is met. In such a manner, the subject's cardiac pulse rate is estimated from video data on a continuous basis.

However, there is a need of improving the conventional video-image physiological information detection method for estimating pulse rates. The above-mentioned patent and patent application publications are incorporated herein by reference for purposes including, but not limited to, indicating the background of the present invention and illustrating the situation of the art.

As is described in greater detail below, the present invention provides a thermal video-image physiological information detection system and method thereof for estimating pulse rates. In a detecting operation, a series of video images of head portions are captured and processed to obtain variations of temperature data and to further convert into pulse rate data in such a way as to improve the estimated pulse rates of the conventional physiological information detection method.

SUMMARY OF THE INVENTION

The primary objective of this invention is to provide a thermal video-image physiological information detection system and method thereof for estimating pulse rates. In a detecting operation, a series of video images of head portions are captured and processed to obtain variations of temperature data and to further convert into pulse rate data, thereby retrieving personal features of physiological information. Advantageously, the thermal video-image physiological information detection system and method of the present invention is successful in retrieving a biological feature and enhancing the accuracy of estimated pulse rates.

The thermal video-image physiological information detection system in accordance with an aspect of the present invention includes:

an image-capturing unit provided to capture a series of images of head portions;

an image-processing unit connected with the image-capturing unit to receive the captured images, with operating the image-processing unit to process the captured images and to seek or trace at least one first head portion area and at least one first neck portion area thereof in the processed images, with further operating the image-processing unit to process the captured images to retrieve first temperature data from the selected first head portion area and the selected first neck portion area of the processed images, with further operating the image-processing unit to convert variations of the first temperature data into estimated first pulse data; and a data-transmitting unit connected with the image-processing unit to transmit the estimated first pulse data to a predetermined device.

In a separate aspect of the present invention, the image-capturing unit is a digital camera or an infrared camera.

In a further separate aspect of the present invention, the image-processing unit is further operated to trace at least one first arterial portion area in the selected first neck portion area.

In yet a further separate aspect of the present invention, the image-processing unit further includes a facial recognition module.

In yet a further separate aspect of the present invention, the facial recognition module is operated to process a procedure of a live detection step, a wavelet frame representation step and a facial candidate selection step with the captured images.

In yet a further separate aspect of the present invention, the predetermined device is a wearable device, a mobile device, a STB device, a display device or a computer device.

In yet a further separate aspect of the present invention, the predetermined device further includes a multiple recognition system.

In yet a further separate aspect of the present invention, the multiple recognition system includes a RFID reader module and a 2D bar code reader module.

In yet a further separate aspect of the present invention, the data-transmitting unit connects with a heterogeneous network via the predetermined device.

The thermal video-image physiological information detection method in accordance with an aspect of the present invention includes:

providing an image-capturing unit to capture a series of images of head portions;

providing an image-processing unit to connect with the image-capturing unit to receive the captured images, with operating the image-processing unit to process the captured images and to seek or trace at least one first head portion area and at least one first neck portion area thereof in the processed captured images, with further operating the image-processing unit to process the captured images to retrieve first temperature data from the selected first head portion area and the selected first neck portion area of the processed images, with further operating the image-processing unit to convert variations of the first temperature data into estimated first pulse data; and providing a data-transmitting unit to connect with the image-processing unit to transmit the estimated first pulse data to a predetermined device.

In a separate aspect of the present invention, the image-processing unit is further operated to trace at least one first arterial portion area in the selected first neck portion area.

In a further separate aspect of the present invention, the image-processing unit is further operated to trace a second head portion area and a second neck portion area thereof in the processed captured images.

In yet a further separate aspect of the present invention, the image-processing unit is further operated to trace a second arterial portion area in the second neck portion area.

In yet a further separate aspect of the present invention, the image-processing unit further includes a facial recognition module to recognize at least one first facial portion area in the first head portion area.

In yet a further separate aspect of the present invention, the facial recognition module is operated to process a procedure of a live detection step, a wavelet frame representation step and a facial candidate selection step for facial recognition.

In yet a further separate aspect of the present invention, the predetermined device is a wearable device, a mobile device, a STB device, a display device or a computer device.

In yet a further separate aspect of the present invention, the predetermined device further includes a multiple recognition system to execute a recognition procedure for identifying personnel to allow operating the predetermined device.

In yet a further separate aspect of the present invention, the multiple recognition system includes a RFID reader module and a 2D bar code reader module for executing the recognition procedure.

In yet a further separate aspect of the present invention, the first head portion area is a round-shaped head portion area, an oval-shaped head portion area or an elliptic head portion area.

Further scope of the applicability of the present invention will become apparent from the detailed description given hereinafter. However, it should be understood that the detailed description and specific examples, while indicating preferred embodiments of the invention, are given by way of illustration only, since various modifications will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1:
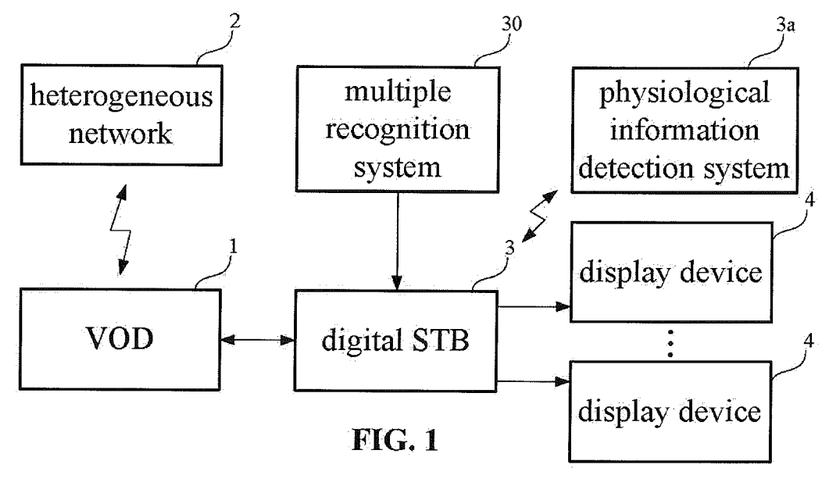
FIG. 1 is a block diagram of a video on demand (VOD) system applied to a thermal video-image physiological information detection system in accordance with a first preferred embodiment of the present invention.

FIG. 1 shows a block diagram of a video on demand (VOD) system applied to a thermal video-image physiological information detection system in accordance with a first preferred embodiment of the present invention. Referring now to FIG. 1, the thermal video-image physiological information detection system in accordance with the first preferred embodiment of the present invention includes a digital STB 3, a multiple recognition system 30 and a physiological information detection system 3a. The multiple recognition system 30 and the physiological information detection system 3a connect and communicate with the digital STB 3.

With continued reference to FIG. 1, the digital STB 3 connects with a heterogeneous network 2 via a video on demand (VOD) system 1 for receiving digital video/audio data. The digital STB 3 connects with a computer system or a smart TV system for storing the digital video/audio data. In a preferred embodiment, the heterogeneous network 2 includes a Wireless LAN system and a 3G/WiMAX system or other equivalent system. The digital STB 3 further connects with a plurality of display devices 4 for displaying the digital video/audio data.

With continued reference to FIG. 1, the digital STB 3 is suitable for processing TV signals, cable signals, satellite signals or broadcast and IP/DSL signals. In a preferred embodiment, the digital STB 3 has a function of bidirectional digital communication or digital multiple-media network communication. The digital STB 3 is also suitable for an ATSC system, a DVB system, an ISDB system, a DMT-T system or an ADTB-T system.

With continued reference to FIG. 1, the digital STB 3 connects between the heterogeneous network 2 and the display devices 4 and other peripherals. Users can operate the digital STB 3 for internet accessing (e.g. e-mailing), website surfing or online shopping via the heterogeneous network 2. In a preferred embodiment, the display device 4 can be a monitor device, a TV device or other peripheral.

With continued reference to FIG. 1, the multiple recognition system 30 connects between the heterogeneous network 2 and the display devices 4 and other peripherals for executing a recognition procedure for identifying personnel to allow operating the digital STB 3 or the display device 4. In a preferred embodiment, the multiple recognition system 30 includes at least two recognition units with various recognition technologies for accomplishing multiple recognition steps.

Figure 2:
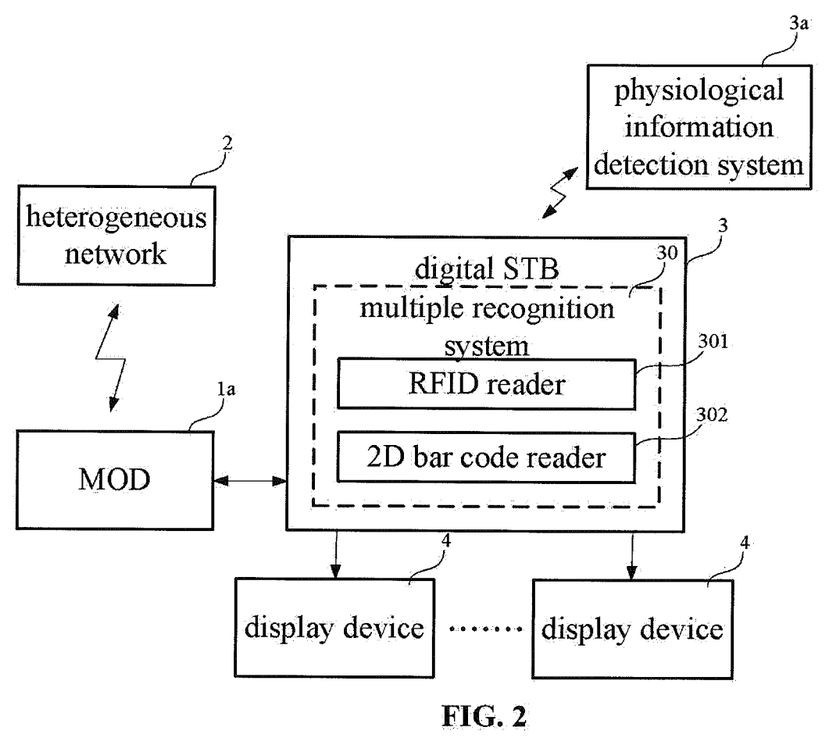
FIG. 2 is a block diagram of a multimedia on demand (MOD) system applied to the thermal video-image physiological information detection system in accordance with a second preferred embodiment of the present invention.

FIG. 2 shows a block diagram of a multimedia on demand (MOD) system applied to the thermal video-image physiological information detection system in accordance with a second preferred embodiment of the present invention corresponding to that shown in FIG. 1. Referring now to FIG. 2, in comparison with the first preferred embodiment, the thermal video-image physiological information detection system of the second preferred embodiment includes a digital STB 3 and a multiple recognition system 30 incorporated therein.

With continued reference to FIG. 2, the multiple recognition system 30 includes a RFID reader module 301 and a 2D bar code reader module 302 or other equivalent reader module (e.g., magnetic card reader or password input). Accordingly, users can be authorized to access one of the VOD systems 1, MOD systems 1a, e-learning systems, medical management systems, bank account systems and online-game systems via the heterogeneous network 2 by operating the multiple recognition system 30.

Figure 3:
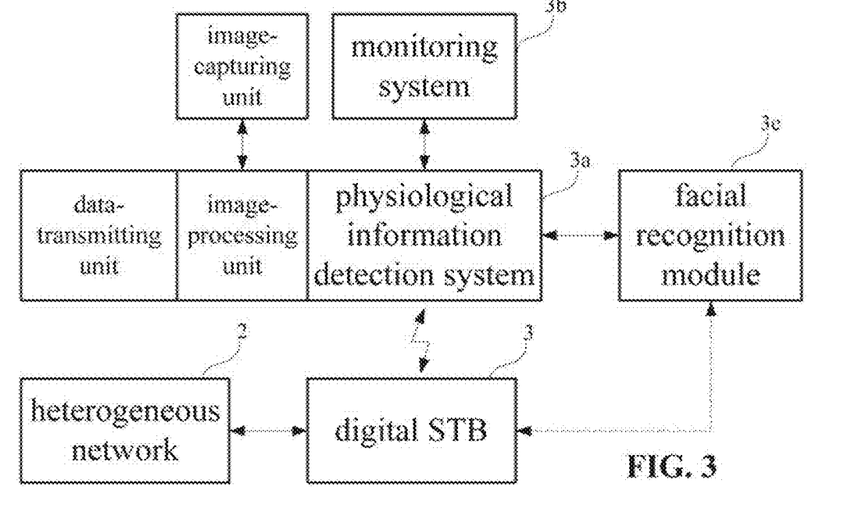
FIG. 3 is a block diagram of the thermal video-image physiological information detection system in accordance with a third preferred embodiment of the present invention.

FIG. 3 shows a block diagram of the thermal video-image physiological information detection system in accordance with a third preferred embodiment of the present invention. Referring now to FIG. 3, in comparison with the first preferred embodiment, the physiological information detection system 3a of the third preferred embodiment includes an image-capturing unit, an image-processing unit and a data-transmitting unit. In a preferred embodiment, the physiological information detection system 3a further connects or online connects with a monitoring system 3b for receiving other images therefrom.

With continued reference to FIG. 3, the image-capturing unit is a camera device or a plurality of camera devices and is provided to capture a series of images of human head portions and peripheral portions thereof. In a preferred embodiment, the images of human head portions are live images while the image-capturing unit is provided in a public place or the like. The image-capturing unit is a digital camera, an infrared camera or other equivalent device (e.g., CCD component installed in a video camera).

Figure 4:
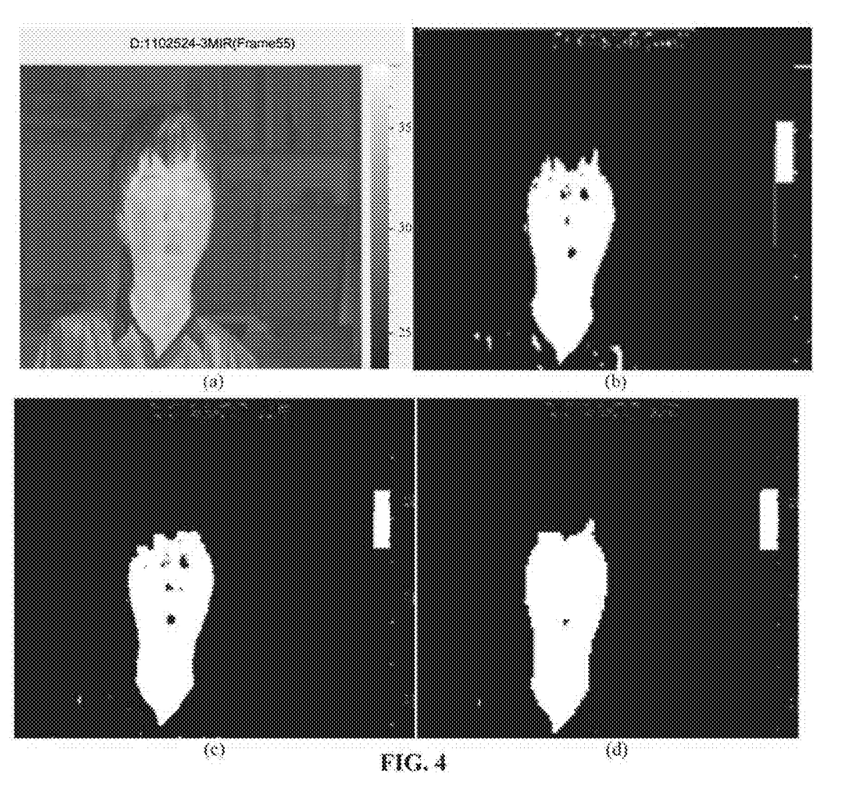
FIG. 4 is a series of images (a)-(d) generated from a captured image preprocessed by the thermal video-image physiological information detection system in accordance with a preferred embodiment of the present invention.

FIGS. 4(a)-4(d) show a series of images generated from a captured image preprocessed by the thermal video-image physiological information detection system in accordance with a preferred embodiment of the present invention. Referring to FIGS. 3 and 4(a), the image-processing unit connects with the image-capturing unit to receive at least one of the captured images. In operation, the image-processing unit is operated to preprocess the captured images to obtain a series of four processed images, as best shown in FIG. 4(a)-4(d). By way of example, FIG. 4(a) shows a gray scale image generated from an original color image; FIG. 4(b) shows a binary image binary-converted from the gray scale image; FIG. 4(c) shows an erosion image generated from the binary image by a morphological operation; and FIG. 4(d) shows a dilation image generated from the binary image by the morphological operation.

Figure 5:
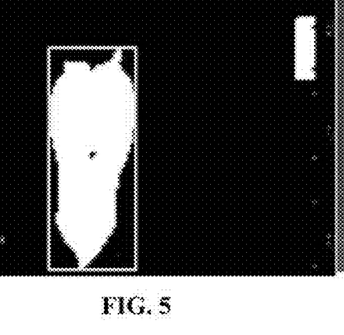
FIG. 5 is a processed image generated from the erosion image and the dilation image calculated by a connected component labeling algorithm applied in the thermal video-image physiological information detection system in accordance with the preferred embodiment of the present invention.

Referring back to FIG. 3, in operation, the image-processing unit is further operated to seek or trace at least one first head portion area and at least one first neck portion area thereof in the processed images. By way of example, FIG. 5 shows a processed image generated from the erosion image and the dilation image, as best shown in FIGS. 4(c) and 4(d), calculated by a connected component labeling (CCL) algorithm applied in the thermal video-image physiological information detection system in accordance with the preferred embodiment of the present invention. Referring to FIGS. 3, 4(d) and 5, pixels of the dilation image are initially scanned from up to down and from left to right to obtain a plurality of blocks. Finally, the blocks are further processed by a CCL algorithm to obtain a bounding box in the bounded image, as best shown in FIG. 5.

Figure 6:
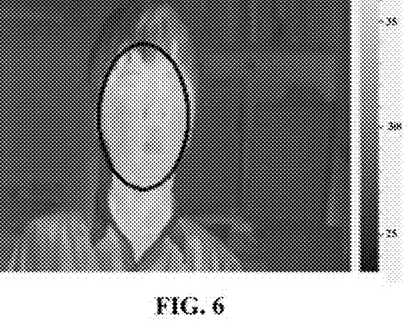
FIG. 6 is another processed image generated from the bounded image to seek or trace a head portion area by the thermal video-image physiological information detection system in accordance with the preferred embodiment of the present invention.

FIG. 6 shows another processed image generated from the bounded image, as shown in FIG. 5, to seek or trace a head portion area by the thermal video-image physiological information detection system in accordance with the preferred embodiment of the present invention. By way of example, the head portion area is a round-shaped head portion area, an oval-shaped head portion area or an elliptic head portion area. Referring to FIGS. 3 and 6, the thermal video-image physiological information detection method includes the step: tracing the elliptic head portion area in the processed images. The elliptic head portion area is s=(xc, yc, b), where (xc, yc) is a center point position and b is a length of minor axis of ellipse. A summation of normalized gradient of an elliptic periphery can be calculated by $$\phi_g(S_i) = \frac{1}{N_b} \sum_{i=1}^{N_b} |g_{s(i)}|$$

-continued $$^*s = \arg\max_{s_i \in S}\{\phi_g(S_i)\}$$

where $\phi_g(S_i)$ is a mean value of gradient of the elliptic periphery, $N_b$ is a total number of pixels at the elliptic periphery, $g_{s(i)}$ is a gradient of pixel i at the elliptic periphery and *s is a maximum weight in the peripheral space.

Furthermore, a tracing position s can be calculated by $$S=\{s: |x-x_c| \leq x_r, |y-y_c| \leq y_r, |b-b_c| \leq b_r\}$$

where $x_r$ and $y_r$ are coordinates of a range for tracing a center point position $(x_c, y_c)$ and $b_r$ is a maximum length of the minor axis of the ellipse.

Accordingly, the physiological information detection system 3a is successful in tracing pixels of the head portion area (or neck portion area), thereby determining the elliptic head portion area, as best shown in FIG. 6. In a preferred embodiment, at least one arterial portion area is further traced in the neck portion area. In the next step, the image-processing unit is further operated to convert variations of the temperature data into estimated pulse data.

Figure 7:
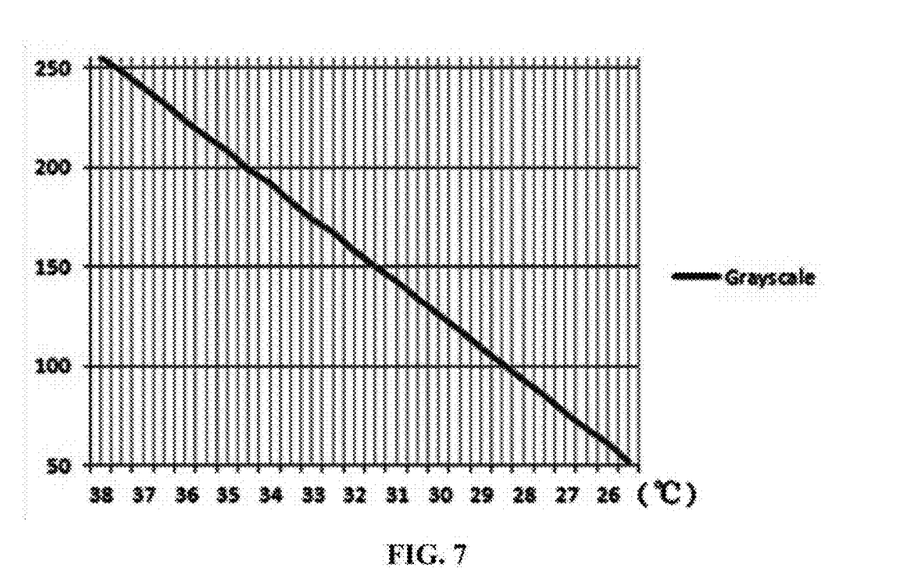
FIG. 7 is a chart diagram illustrating grayscale values in relation to temperatures applied in the thermal video-image physiological information detection system in accordance with the preferred embodiment of the present invention.

Referring back to FIG. 3, the image-processing unit is further operated to process the captured images to retrieve temperature data from the head portion area and the neck portion area of the processed images. By way of example, FIG. 7 shows a chart illustrating grayscale values in relation to temperatures applied in the thermal video-image physiological information detection system in accordance with the preferred embodiment of the present invention. Referring to FIGS. 3 and 7, the physiological information detection system 3a is operated to calculate temperatures of pixels of the elliptic head portion area by the equation:

Temperature=(260-grayscale pixels)×calibration constant+$T_b$ where the calibration constant is 0.02326, and $T_b$ is a systematical lowest temperature.

Figure 8:
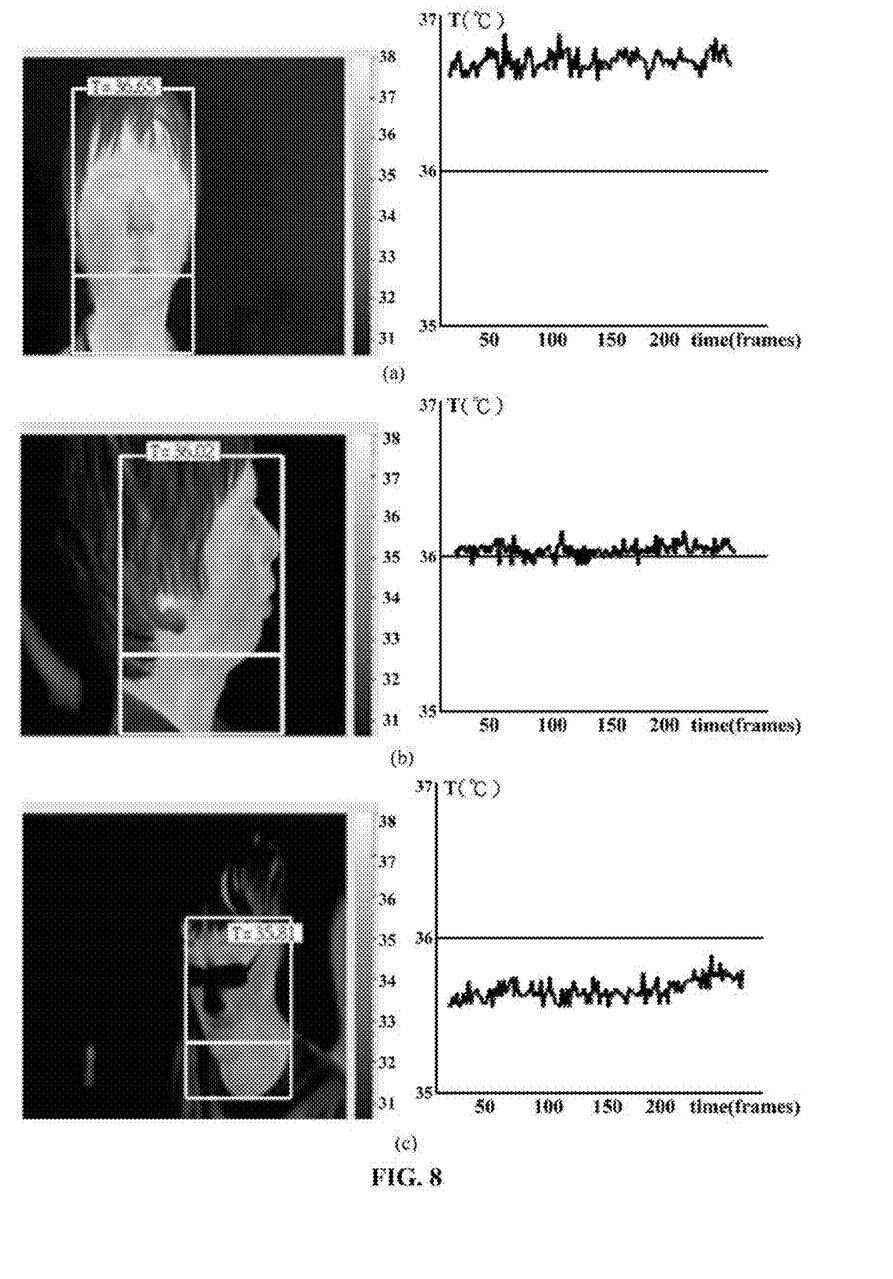
FIG. 8 are image views (a)-(c) of the head portion area from three different angles and three chart diagrams of temperatures versus time thereof processed by the thermal video-image physiological information detection system in accordance with the preferred embodiment of the present invention.

FIGS. 8(a)-8(c) show (live) image views of the head portion area from three different angles (i.e., front view, right view and left front view of three people) and three chart diagrams of temperatures versus time thereof processed by the thermal video-image physiological information detection system in accordance with the preferred embodiment of the present invention. As best shown in left portions of FIGS. 8(a)-8(c), the head portion area and the neck portion area have a preferred bounding box with a ratio of 7:3 for calculating temperatures of the head portion and the neck portion. As best shown in right portions of FIGS. 8(a)-8(c), three chart diagrams of temperatures versus time are calculated from the head portion area and the neck portion area.

Figure 9:
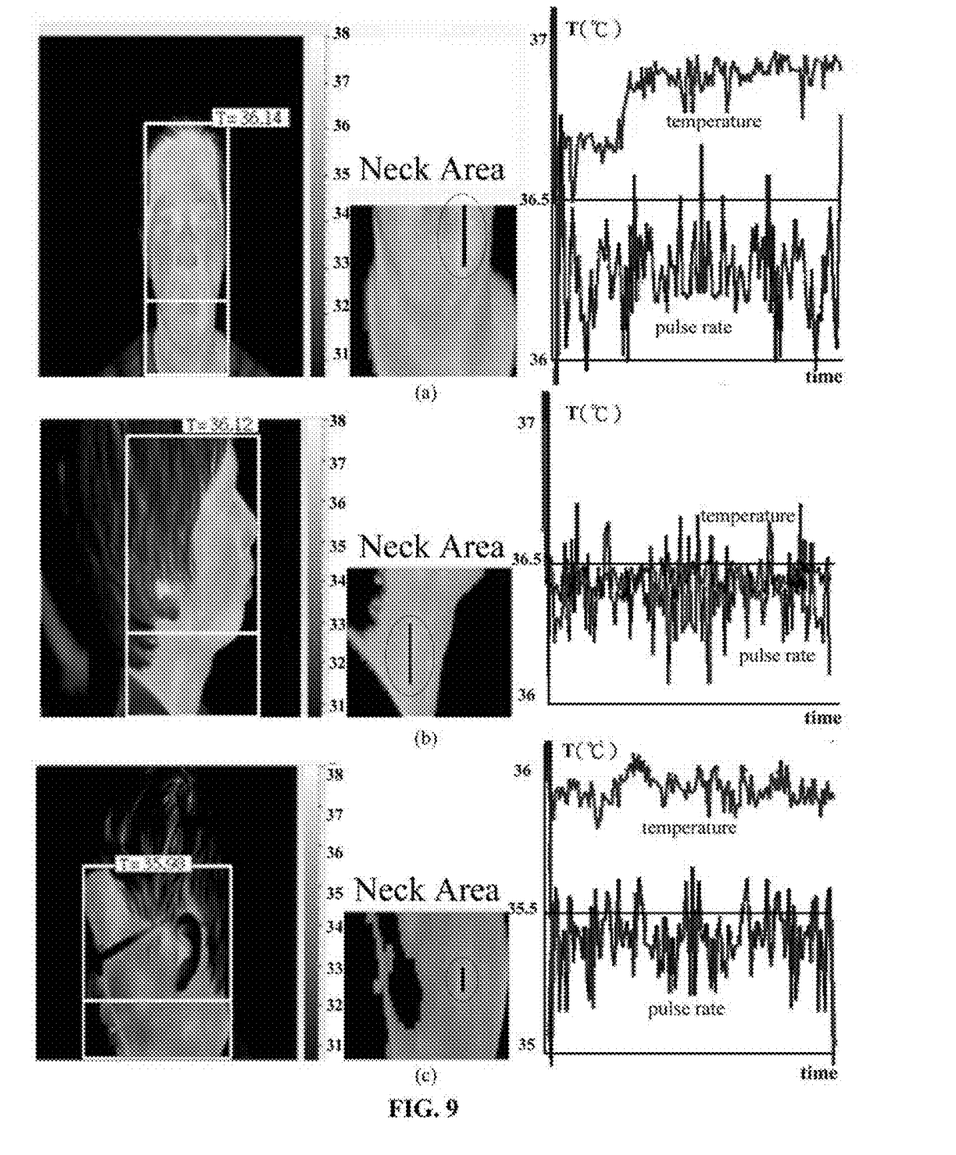
FIG. 9 are image views (a)-(c) of the head portion area from three different angles, three images of corresponding selected neck portion area and three chart diagrams of temperatures versus time and estimated pulse rate thereof processed by the thermal video-image physiological information detection system in accordance with the preferred embodiment of the present invention.

FIGS. 9(a)-9(c) show (live) image views of the head portion area from three different angles (i.e., front view, right view and left view of three people), three images of the corresponding selected neck portion area and three chart diagrams of temperatures versus time and estimated pulse rate thereof processed by the thermal video-image physiological information detection system in accordance with the preferred embodiment of the present invention. As best shown in left portions of FIGS. 9(a)-9(c), the head portion areas and the neck portion areas are successfully traced in the processed images. As best shown in middle portions of FIGS. 9(a)-9(c), the arterial portion areas are further successfully traced in the neck portion areas, as indicated at an ellipse region in FIGS. 9(a)-9(c). As best shown in upper right waveforms of FIGS. 9(a)-9(c), three chart diagrams of temperatures versus time are calculated from the head portion area and the neck portion area. As best shown in lower right waveforms of FIGS. 9(a)-9(c), three chart diagrams of estimated pulse rate are automatically converted from the temperatures of head portion area and the neck portion area by a Fourier transform method or other equivalent transform method.

In another embodiment, the image-processing unit is further operated to trace another head portion area and another neck portion area thereof in the processed images synchronously, as best shown in FIGS. 8(a)-8(c) and 9(a)-9(c). Moreover, the image-processing unit is further operated to trace another arterial portion area in another neck portion area.

Referring back to FIG. 3, the data-transmitting unit is a short-range communication device or other equivalent device. In a preferred embodiment, the short-range communication device is a Zigbee module, a Bluetooth module, a near field communication (NFC) or a high-frequency RFID module or other equivalent module. The data-transmitting unit connects with the image-processing unit to transmit the estimated pulse (or pulse rate) data to a predetermined device.

With continued reference to FIG. 3, the image-processing unit further connects with a facial recognition module 3c to recognize a facial portion area in the head portion area. In a preferred embodiment, image-processing unit is operated to trace a middle portion or a T portion in the facial portion area. In the recognition operation, the facial recognition module 3c is operated to process a procedure of a live detection step, a wavelet frame representation step and a facial candidate selection step for facial recognition.

Although the invention has been described in detail with reference to its presently preferred embodiments, it will be understood by one of ordinary skill in the art that various modifications can be made without departing from the spirit and the scope of the invention, as set forth in the appended claims.

What is claimed is:

1. A physiological information detection system comprising:
   an image-capturing unit provided to capture a series of images of head portions;
   an image-processing unit connected with the image-capturing unit to receive the captured series of images, with the image-processing unit configured to process the captured images and to seek or trace at least one first head portion area and at least one first neck portion area thereof in the processed captured series of images, with the at least one first head portion area having a periphery, with tracing the at least one first head portion area $s=(x_c, y_c, b)$, where $(x_c, y_c)$ is a center point position and b is a length of a minor axis of the at least one first head portion area, with the image processing unit configured to calculate a summation of a normalized gradient of the periphery of the at least one first head portion area with:

$$\phi_g(S_i) = \frac{1}{N_b}\sum_{i=1}^{N_b}|g_{s(i)}|$$

$$^*s = \arg\max_{s_i \in S}\{\phi_g(S_i)\}$$

where $\phi_g(S_i)$ is a mean value of a gradient of the periphery, $N_b$ is a total number of pixels at the periphery, $g_{s(i)}$ is a gradient of pixel i at the periphery and *s is a maximum weight in a peripheral space, to define the periphery of the at least one first head portion area in the captured series of images, with the image-processing unit further configured to process the captured series of images to retrieve first temperature data from the at least one first head portion area and the at least one first neck portion area of the processed captured series of images, with the image-processing unit also configured to convert variations of the first temperature data into estimated first pulse data; and a data-transmitting unit connected with the image-processing unit to transmit the estimated first pulse data to a predetermined device.

2. The system as defined in claim 1, wherein the image-capturing unit is a digital camera or an infrared camera.

3. The system as defined in claim 1, wherein the image-processing unit is further configured to trace at least one first arterial portion area in the at least one first neck portion area.

4. The system as defined in claim 1, wherein the image-processing unit further includes a facial recognition module.

5. The system as defined in claim 4, wherein the facial recognition module is configured to process a procedure of a live detection step, a wavelet frame representation step and a facial candidate selection step with the captured series of images.

6. The system as defined in claim 1, wherein the predetermined device is a wearable device, a mobile device, a STB device, a display device or a computer device.

7. The system as defined in claim 1, wherein the predetermined device further includes a multiple recognition system.

8. The system as defined in claim 7, wherein the multiple recognition system includes a RFID reader module and a 2D bar code reader module.

9. The system as defined in claim 1, wherein the data-transmitting unit connects with a heterogeneous network via the predetermined device.

10. The system as defined in claim 1, wherein the image-processing unit is further configured to trace a second head portion area and a second neck portion area thereof in the processed captured series of images.

11. A physiological information detection method comprising:

providing an image-capturing unit capturing a series of images of head portions;

providing an image-processing unit connected with the image-capturing unit receiving the captured series of images, with the image-processing unit processing the captured series of images and seeking or tracing at least one first head portion area and at least one first neck portion area thereof in the processed images, with at least first head portion area having a periphery;

tracing the at least one first head portion area $s=(x_c, y_c, b)$, where $(x_c, y_c)$ is a center point position and b is a length of minor axis of the at least one first head portion area;

calculating a summation of a normalized gradient of the periphery of the at least one first head portion area with:

$$\phi_g(S_i) = \frac{1}{N_b} \sum_{i=1}^{N_b} |g_{s(i)}|$$

$$*s = \arg\max_{s_i \in S} \{\phi_g(S_i)\}$$

where $\phi_g(S_i)$ is a mean value of the gradient of the periphery, $N_b$ is a total number of pixels at the periphery, $g_{s(i)}$ is a gradient of pixel i at the periphery, and *s is a maximum weight in a peripheral space, to define the periphery of the at least one first head portion area in the captured series of images;

processing the captured series of images to retrieve first temperature data from the selected at least one first head portion area and the selected at least one first neck portion area of the processed captured series of images;

converting variations of the first temperature data into estimated first pulse data; and providing a data-transmitting unit connecting with the image-processing unit to transmit the estimated first pulse data to a predetermined device.

12. The method as defined in claim 11, further comprising tracing at least one first arterial portion area in the at least one first neck portion area.

13. The method as defined in claim 11, further comprising tracing a second head portion area and a second neck portion area thereof in the processed captured series of images.

14. The method as defined in claim 13, further comprising tracing a second arterial portion area in the second neck portion area.

15. The method as defined in claim 11, further comprising recognizing at least one first facial portion area in the at least one first head portion area by a facial recognition module.

16. The method as defined in claim 15, wherein the facial recognition module processes a procedure of a live detection step, a wavelet frame representation step and a facial candidate selection step for facial recognition.

17. The method as defined in claim 11, wherein the predetermined device is a wearable device, a mobile device, a STB device, a display device or a computer device.

18. The method as defined in claim 11, wherein the predetermined device further includes a multiple recognition system executing a recognition procedure for identifying personnel to allow operating the predetermined device.

19. The method as defined in claim 18, wherein the multiple recognition system includes a RFID reader module and a 2D bar code reader module executing the recognition procedure.

20. The method as defined in claim 11, wherein the at least one first head portion area is a round-shaped head portion area or an oval-shaped head portion area.

* * * * *